United States Patent
Pereira et al.

(10) Patent No.: US 9,295,706 B2
(45) Date of Patent: Mar. 29, 2016

(54) **PHYTOTHERAPIC PHARMACEUTICAL COMBINATION OF *LIPPIA SALVIIFOLIA* AND *LIPPIA SIDOIDES*, PHYTOTHERAPIC PHARMACEUTICAL COMPOSITION, PROCESS FOR PREPARING A PHYTOTHERAPIC PHARMACEUTICAL COMPOSITION AND VETERINARY USES THEREOF**

(76) Inventors: Ana Maria Soares Pereira, Ribeirao Preto (BR); Suzelei de Castro Franca, Ribeirao Preto (BR); Ana Lucia Fachin, Ribeirao Preto (BR); Bianca Waleria Bertoni, Ribeirao Preto (BR); Edieidia Souza Pina, Pradopolis (BR); Juliana da Silva Coppede, Ribeirao Preto (BR)

( * ) Notice: Subject to any disclaimer, the term of this patent is extended or adjusted under 35 U.S.C. 154(b) by 111 days.

(21) Appl. No.: 13/997,814

(22) PCT Filed: Feb. 10, 2011

(86) PCT No.: PCT/BR2011/000005
§ 371 (c)(1),
(2), (4) Date: Jun. 25, 2013

(87) PCT Pub. No.: WO2012/088568
PCT Pub. Date: Jul. 5, 2012

(65) Prior Publication Data
US 2013/0280353 A1    Oct. 24, 2013

(30) Foreign Application Priority Data
Dec. 27, 2010 (BR) ........................................ 005541

(51) Int. Cl.
*A61K 36/85* (2006.01)
*A61K 36/185* (2006.01)
*A23K 1/16* (2006.01)
*A23K 1/18* (2006.01)

(52) U.S. Cl.
CPC .................. *A61K 36/85* (2013.01); *A23K 1/164* (2013.01); *A23K 1/1609* (2013.01); *A23K 1/1612* (2013.01); *A23K 1/1646* (2013.01); *A23K 1/1813* (2013.01)

(58) Field of Classification Search
None
See application file for complete search history.

(56) References Cited

U.S. PATENT DOCUMENTS 8,119,162 B2 *   2/2012   Miksa et al. .................. 424/489

FOREIGN PATENT DOCUMENTS

CN   101744833 A   *   6/2010
RU   2147438 C1   *   4/2000

OTHER PUBLICATIONS

Botelho (Antimicrobial activity of the essential oil from Lippiasidoides, carvacrol and thymol against oral pathogens, Brazilian Journal of Medical and Biological Research (2007) 40, 349-356.*
Silva (Chemical composition of the essential oil and hexanic fraction of Lippia and Lantana species, Revista Brasileira de Farmacognosia Brazilian Journal of Pharmacognosy 20(6): 843-849, Dez 2010).*

* cited by examiner

*Primary Examiner* — Chris R Tate
*Assistant Examiner* — Randall Winston
(74) *Attorney, Agent, or Firm* — Laurence P. Colton; Smith Tempel Blaha LLC

(57) ABSTRACT

Phytotherapic pharmaceutical forms with antimicrobial activity, comprising a mixture of essential oils of *Lippia salviifolia* and *Lippia sidoides*, appropriate for the treatment of mastitis, notably bovine mastitis, and to a process of preparation of said compositions and their veterinary uses.

6 Claims, No Drawings

PHYTOTHERAPIC PHARMACEUTICAL COMBINATION OF *LIPPIA SALVIIFOLIA* AND *LIPPIA SIDOIDES*, PHYTOTHERAPIC PHARMACEUTICAL COMPOSITION, PROCESS FOR PREPARING A PHYTOTHERAPIC PHARMACEUTICAL COMPOSITION AND VETERINARY USES THEREOF

FIELD OF THE INVENTION

The present invention refers to phytotherapic pharmaceutical forms with antimicrobial activity, comprising a mixture of essential oils of *Lippia salvifolia* and *Lippia sidoides*. Said composition is especially appropriate to treat mastitis, notably bovine mastitis. The present invention also refers to the process of preparation of said compositions and their veterinary uses.

Particularly, the veterinary pharmaceutical composition object of the present invention comprises, as an active ingredient, a mixture of essential oils of *Lippia salvifolia* and *Lippia sidoides* in balanced ratios in terms of the average content of thymol and carvacrol in said mixture.

BACKGROUND OF THE INVENTION

Bovine mastitis is considered as the disease causing the largest economic loss to milk production, due to the reduction of quantity and compromise to the quality of the produced milk, or even for the full loss of secreting capacity of the mammary gland. Mastitis is a mammary gland inflammation, usually of infectious nature, which may be considered as clinical or subclinical. Clinical mastitis has clear signs, such as edema, increase in temperature, hardening, pain in the mammary gland, grains, pus or any change in milk characteristics. In the subclinical form of mastitis, no macroscopic changes are seen, but rather changes in milk composition, i.e., there are no visible signs of udder inflammation.

In Brazil, subclinical mastitis is highly incident, with indexes between about 45 and 97.00% of bovine stocks and the reduction in milk production is of about 25-43.0%. This is a considerable figure, and worrying for the national milk industry.

Ethyology of mastitis is complex and multiple, wherein the main ethyological agents are bacteriae from genus *Staphylococcus* and *Streptococcus*. Mastitis can be classified as contagious or environmental, wherein the first one is mainly caused by *Staphylococcus aureus, S. epidermidis, Streptococcus agalactiae, S. dysgalactiae, Corynebacterium bovis* and *Actinomyces pyogenes*, which are responsible for about 80% of mastitis cases. In environmental mastitis, the main agents include *Escherichia coli, Klebsiella pneumoniae, Enterobacter aerogenes, Streptococcus faecium, Nocardia* spp and *Pseudomonas aeruginosa*.

Besides being the most important sanitary problem as related to milk production, mastitis, as indicated above, is also responsible for large economical losses caused by the reduction in the quality and quantity of milk, costs with medicine, veterinary care and the substitution of breeding animals.

In the past few years, plants have been more and more highlighted as the main targets for scientific studies, with a large variety of structures, chemical properties and biologically active substances. Many vegetal species have given significant contributions to the development and synthesis of new pharmaceuticals. Brazil is considered so far as the country with the most varied genetic diversity in the world, with about 55,000 catalogued species from an estimated total between 350,000 and 550,000 species. For this reason, scientific research in the botanical, agronomical, phytochemical, genetic and pharmacological areas have increased in an attempt to search and validate bioactive compounds for therapeutic purposes.

Microorganism resistance and side effects caused by the continued use of synthetic medicines take the population to search for natural products. Also, phytotherapics have synergy between components as present in the plant with their action and, since they have a large number of substances, they work against different molecular targets, thus causing less side effects. Furthermore, since the costs for research and development for phytotherapic medicines are much lower than those related to synthetic medicines, they are more accessible and the number of phytotherapics is largely increasing in the market nowadays.

Another aspect to be considered is the increase in microorganism resistance to clinical antibiotics, which requires the development of new drugs. For this reason, studies on aromatic medicinal plants with therapeutic potential have recently increased, mainly due to the proved antimicrobial action of monoterpene compounds as present in essential oils.

Genus *Lippia* has been intensively studied from the ethnobotanic, chemical and pharmacological point of view. Results from these studies have confirmed anti-inflammatory, larvicide, hypotensive, sedative, analgesic, carminative, antimicrobial, cytotoxic, antioxidant and other pharmacological activities.

Among *Lippia* species available in Brazil, we highlight: *Lippia alba*, which essential oil contains about 40% carvone and has bactericidal activity against gram positive bacteriae; *Lippia javanica* rich in micernone (36-62%), carvone (61-73%), piperitenone (32-48%), ipsenone (42-61%) and linalool (>65%), depending on the growing environment, efficient against the growth of microorganisms *Cryptococcus neoformans, Bacillus cereus, Escherichia coli* and *Staphylococcus aureus*, having bacteriostatic effect against *Klebsiella pneumoniae* and *Plasmodium falparium* in micromolar concentrations; *Lippia multiflora* having antioxidant and antimicrobial activity against *Pseudomonas aeruginosa* and *Candida albicans*, which action is attributed to carvacrol, one of the major components of the essential oil of that species; *Lippia dulcis*, which in vivo study performed with swines has shown that the essential oil in 100 µg/ml concentration has anti-histaminergic and anticholinergic activities.

Studies as mentioned above related to antimicrobial activities have emphasized thymol and carvacrol as present in genus *Lippia*, highlighting *Lippia sidoides* with high yield of essential oil.

More specifically, such pharmacological studies have confirmed the therapeutic potential of *Lippia sidoides*, including: confirmed cytotoxic activity over three kinds of cancer cells, i.e. HL60 (leukemia), SW1573 (lung carcinoma) and CEM (lymphoblastic leukemia); anti-inflammatory activity of *L. sidoides* oil in an experiment with rats; inhibition of the activity of the acetylcholinesterase enzyme indicating potential use in the treatment of Alzheimer; antioxidant activity of thymol and carvacrol as present in its oil; efficacy in the reduction of dental plaque, gingivitis and gum bleeding; antimicrobial activity against *S. aureus, C. albicans* and *E. coli*; antifungal activity against *Candida albicans, Candida tropicalis* and *Microsporum canis*; antimicrobial activity against gram-positive and gram-negative bacteriae; bacteriostatic activity against various strains of isolated *S. aureas* from clinical material, resistant to antibiotics; anti-helminths activity, besides having larvicidal activity in the combat against *A. aegypti* mosquitoes.

To yield a medicine produced from plants synthesizing essential oils, preliminary agronomic research is required, so to supply yielding data as a function of given edaphic and seasonality conditions. The content of essential oil in a plant may vary as a function of the time of the year, stage of development, geographic and ecological factors, as well as genetic variations. Botanically identical plants may be chemically different from each other and, when it happens, they are called chemotypes or chemical races. Chemical variations are characterized by the majority of given compounds in essential oils, which are called major components.

Studies performed by various researchers have shown that *L. sidoides* present variations in content and quality of oil depending on the place of origin. This data is summarized on Table 1 below.

TABLE 1

Composition of essential oil in different chemotypes of *L. sidoides*

| Component | Chemotypes (% content) | | | | | | | |
|---|---|---|---|---|---|---|---|---|
| | a | b | c | d | e | f | g | h |
| Thymol | 56.67 | 66.67 | 59.65 | 59.65 | 43.5 | 80.8 | 66.67 | 48.32 |
| Carvacrol | 16.73 | 1.81 | | | 4.3 | | | 6.90 |
| p-Cymene | 7.13 | 7.13 | | | | 8.6 | 7.13 | |
| Thymol methyl ether | 5.06 | 1.15 | 1.79 | | | | 1.15 | 1.34 |
| Aromadendrene | 2.79 | | 0.53 | | | | | 1.81 |
| 1.8-Cyneol | 2.39 | 1.39 | | | | 1.3 | 1.39 | 8.62 |
| γ-Elemene | 2.28 | | | | | | 1.81 | |
| γ-Terpinene | 1.42 | 1.13 | 3.83 | 3.83 | | 1.6 | 4.06 | 0.58 |
| α-Terpinene | 1.12 | | 1.43 | 1.43 | | | 1.13 | 0.12 |
| β-Myrcene | 0.86 | 1.76 | 5.43 | 5.43 | 6.5 | 0.9 | 1.76 | 0.32 |
| α-Tujone | 0.78 | 0.73 | 1.48 | 1.48 | | | 0.73 | |
| Octen-3-ole | 0.51 | 0.81 | | | | | 0.81 | 0.37 |
| p-Cymene | | 7.13 | 9.08 | 9.08 | 8.6 | | | 1.38 |
| E-Caryophyllene | | 11.73 | 10.60 | | | | | |
| Limonene | | | 1.01 | 1.01 | | | | |
| Di-hydro-aromadendrene | | | 0.91 | | | | | |
| Caryophyllene Oxide | | | 0.72 | | | | | 1.88 |
| α-Copaene | | | 0.66 | | | | | 0.26 |
| α-Humulene | | | 0.56 | | | | | 0.65 |
| α-Pinene | | | 0.51 | 0.51 | | | | 0.17 |
| α-Muurolene | | | 0.45 | | | | | |
| δ-Cadinene | | | 0.35 | | | | | 0.59 |
| Linalool | | | 0.28 | 0.28 | | | | |
| β-Ocymene | | | 0.27 | 0.27 | | | | 0.50 |
| Umbellulone | | | | 0.46 | | | | 0.22 |
| Methyl thymylether | | | | 1.79 | | | | |
| β-Caryophyllene | | | | | 9.7 | | 11.73 | |
| α-phelandrende | | | | | 22.4 | | | |
| Trans-caryophyllene | | | | | 5.1 | | | 13.77 |
| Trans-miroxide | | | | | | | | 1.32 |
| 4-Terpineol | | | | | | | | 1.34 |
| α-Terpineol | | | | | | | | 2.27 |
| Eugenol | | | | | | | | 0.49 |
| γ-Muurolene | | | | | | | | 0.26 |
| α-Selynene | | | | | | | | 1.72 |

Besides essential oil, various other compounds have been isolated from *L. sidoides*, such as 3-O-acetyloleanolic acid, 3.4 menthol di-hydroxybenzoate, lapachonol, techomaquinone, tectol, tectol acetylate, tectoquinone, quercetin, luteolin, glucoluteolin, taxifolin, isolariciresinol, prenylated naphthoquinone, lipsidoquinone, isocatalpanol and techomaquinone.

There is no information in the literature on similar studies and experiments performed with the species *Lippia salvifolia*.

DISCLOSURE OF THE INVENTION

Therefore, the present invention refers to the viabilization of a phytotherapic pharmaceutical association between essential oils of the vegetal species *Lippia salvifolia* and *Lippia sidoides*, for the production of a veterinary medicine for the control of microorganisms, notably *Escherichia coli, Staphylococcus aureus, Pseudomonas aeruginosa, Staphylococcus epidermidis* and *Candida albicans*.

In particular, the present invention refers to a phytotherapic pharmaceutical composition, which active ingredient is an essential oil obtained from the vegetal species *Lippia salvifolia* and *Lippia sidoides*, for the production of a veterinary medicine for the control of microorganisms, notably *Escherichia coli, Staphylococcus aureus, Pseudomonas aeruginosa, Staphylococcus epidermidis* and *Candida albicans*, or their mixtures.

The present invention also refers to a process for the production of said composition and its veterinary uses for the treatment of mastitis, with effective antimicrobial action.

In this sense, and according to the present invention, various studies and experiments have been performed with essential oils of *Lippia salvifolia* and *Lippia sidoides* to quantitatively define the measurements of said association, so to reach maximum yield in terms of concentration of the components thymol and carvacrol in the resulting oil.

According to the present invention, said studies and experiments have been performed with a pharmaceutical form made with different concentrations of active ingredients, wherein, by means of pre-clinical in vitro and in vivo studies, we have concluded that the most efficient concentration for the control of mastitis agents comprises at least 50% thymol and 5% carvacrol in the essential oil resulting from the association between essential oils of *Lippia salvifolia* and *Lippia sidoides*.

Usually, but not as a limitation, minimum proportions of 50% thymol and 5% carvacrol are reached in mixtures of essential oils of *Lippia salvifolia* and *Lippia sidoides* between 9:1 and 1:9. This ratio depends on the place of growing of the species *Lippia salvifolia* and *Lippia sidoides*.

Table 2 below shows the proportional relationship between major chemical components thymol and carvacrol in a non-limitative or restrictive example of grown species of *Lippia salvifolia* and *Lippia sidoides*, as per studies and experiments as mentioned.

TABLE 2

Content of thymol and carvacrol from species of *Lippia salvifolia* and *L. sidoides*

| | Species | | |
|---|---|---|---|
| Major components | *L. salvifolia* | *L. sidoides* | *L. salvifolia* × *L. sidoides* (9:1) |
| Thymol (%) | 81.91 | 2.10 | 54.47 |
| Carvacrol (%) | 1.82 | 57.38 | 6.21 |

Table 3 below shows Minimum Inhibitory Concentration (MIC) values, expressed in μg/ml, of antibiotics of essential oils in a non-limitative, non-restrictive example of grown species of *Lippia salvifolia* and *Lippia sioides* and their mixtures in 9:1 ratio, in comparison with strains of *Escherichia coli* and *Staphylococcus aureus, Pseudomonas aeruginosa, Staphylococcus epidermidis* and *Candida albicans*.

TABLE 3

MIC Values

| Microorganism | *L. salvifolia* | *L. sidoides* | Mixture (9:1) | Antibiotic |
|---|---|---|---|---|
| *Escherichia coli* | 0.63 | 1.25 | 0.37 | 75 (a) |
| *Staphylococcus aureus* | 0.37 | 0.63 | 0.37 | 75 (a) |
| *Pseudomonas aeruginosa* | 0.37 | 0.37 | 0.37 | 37 (a) |
| *Staphylococcus epidermidis* | 0.63 | 0.63 | 0.37 | 150 (a) |
| *Candida albicans* | 2.50 | 2.50 | 1.25 | 3.15 (b) |

(a) = Gemtamicin
(b) = Amphotericin B

The phytotherapic composition object of the present invention comprises, as an active ingredient, a full amount of essential oil of *Lippia sidoides* and *Lippia salvifolia* varying between 0.1 and 10.0% by weight, preferably varying between 0.5 and 2.0% by weight, and pharmaceutically acceptable vessels and excipients.

This range of active ingredient of essential oil of *Lippia sidoides* and *Lippia salvifolia* provides the supply of at least 50% thymol and at least 5% carvacrol, thus guaranteeing effective microbial action.

The phytotherapic pharmaceutical composition of the present invention also comprises pharmaceutically acceptable ingredients and vessels, liable to clinical and pharmacological dosage, thus being particularly useful for the treatment of bovine mastitis, reducing the quantity and quality of the milk as produced by the mammary gland of the animal.

The present invention also refers to the process of preparation of the phytotherapic pharmaceutical composition, as well as its application for the treatment of bovine mastitis.

The process of the present invention comprises the basic steps below:
a) drying the vegetal material from the species *Lippia sidoides* and *Lippia salvifolia* in a circulating air oven at about 43° C.;
b) hydrodistillation of the material for a 90-minute period;
c) separation of the hydrolate compound by decantation;
d) quantification of the thymol/carvacrol ratio; and
e) addition of the other pharmaceutical vessels and excipients.

The quantification of the thymol/carvacrol ratio in essential oil of *Lippia sidoides* and *Lippia salvifolia*, according to the process of the present invention, may be performed by means of an analytical gas chromatography method linked to mass spectrometry. Conditions for analysis usually include a capillary column DB-5 (30 m×0.25 mm×0.25 μm), an injector at 240° C.; Detector: 230° C., electron impact 70 eV, flowing gas He, flow of 1.0 ml/min, 1/20 split, temperature schedule between 60° C. and 240° C., 3° C./minute, injection volume, 1 μl solution (1 μl essential oil/1 ml hexane).

Furthermore, according to the process of the present invention, the identification of substances from essential oil of *Lippia sidoides* and *Lippia salvifolia* can be performed by comparing their mass spectra with the databank of the Gas Chromatography system linked to Mass Spectrometry (Nist 62 lib.) and kovat retention index.

Non-limitatively and non-exclusively, phytotherapic pharmaceutical compositions of the present invention comprise, in weight by weight percentages, 0-99.89% by weight of emollients/solvents, 0.01-10.0% of antioxidants, 0.10-80% of thickneres, 0.10-50.0% of surfactants, 0-10.0% of preserving/antimicrobial agents, 0-70% of humectants, and 0.01-10% of pH correction agents.

The phytotherapic pharmaceutical composition of the present invention may be prepared as an ointment, solution, emulsion, gels, sprays, creams and any other form which may be applied through the teat canal of the animal.

Preferably, the phytotherapic pharmaceutical composition of the present invention may be prepared as one of the forms as specified below:

Gel Formulation

| | | |
|---|---|---|
| Active ingredient | 0.10-10.00% | Essential oil of *Lippia salvifolia* and *Lippia sidoides* |
| Thickeners | 0.05-40.00% | synthetic polymers such as sodium and calcium carboxymethylcellulose; hydroxyethylcellulose and derivatives; polyvinylpirrolidone; polymers and copolymers derived from acrylic acid and polycrylamide; ethoxylated polyethylene glycol; natural polymers such as gums: xantan, gellan, carrageen, *acacia*, guar, sclerotium, carob bean; pectin; alginate; aluminum silicate and derivatives; agar; gelatin. |
| Solvents | 1.00-99.73% | alcohols and/or water |
| Surfactants | 0.10-50.00% | ethoxylated oils of natural and synthetic origin; derivatives of polyvinyl alcohol; ethoxylated lanolin alcohols; polyoxyethylenes and their derivatives (alkyl ester, stearate, sorbitan fatty ester, castor oil); sorbitan fatty ester; poloxamers; ethoxylated polyethylene glycols; ethoxylated, propoxylated, sulphated, phosphated and carbonated acids (and salts), alcohols and their condensates (ester and ether); amine and amide derivatives; aminoacid derivatives; alkylglycoside, lecithin, cholesterol; saponine derivatives. |
| Preserving/ antimicrobial agents | 0.00-10.00% | benzyl alcohol; parabens; benzalkonium chloride; benzethonium chloride; bronopol; cetrimid; chlorobutanol; phenoxyethanol; imidazolidinyl urea; isothiazolinone; hydantoin DMDM; benzoic, sorbic acids and their derivatives; dehydroacetic acid; ferulic acid; natural preserving agents such as essential oils |
| Humectants | 0.00-70.00% | natural and synthetic glycols; lactic acid |
| Antioxidants | 0.01-10.00% | butyl hydroxide anisol (BHA), butyl hydroxide toluene (BHT), disodium and tetrasodium EDTA; propyl gallate; sodium metabisulphite; antioxidants of vegetal origin such as tocopherols, phenolic acids, ascorbic acids and their derivatives, citric acid, lecithins and plant extracts such as rosemary and *Lippia* |
| pH correcting agents | 0.01-10.00 | acids and bases of natural and synthetic origin |

Emulsion Formulation and Derivatives (Microemulsion, Nanoemulsion, Etc.)

| | | |
|---|---|---|
| Active ingredient | 0.10-10% | Essential oil of *Lippia salvifolia* and *Lippia sidoides* |
| Thickeners | 0.10-70.00% | fatty acids, fatty alcohols and their condensates (ester and ether) of natural and synthetic origin (above 16 carbons); amide; natural and synthetic waxes such as beewax, candelilla, carnauba and ozokerite; paraffin; ethoxylated polyethylene glycol; hydrogenated natural and synthetic oils; synthetic polymers such as sodium and calcium carboxymethylcellulose; hydroxyethylcellulose and derivatives; polyvinylpyrrolidone; polymers and copolymers derived from acrylic acid and polyacrylamide; natural polymers such as gums: xantan, gellan, carrageen, *acacia*, guar, sclerotium, carob bean; pectin; alginate; aluminum silicate and derivatives; agar; gelatin. |
| Surfactants | 0.10-50.00% | ethoxylated oils of natural and synthetic origin; derivatives of polyvinyl alcohol; ethoxylated lanolin alcohols; polyoxyethylenes and their derivatives (alkyl ester, stearate, sorbitan fatty ester, castor oil); sorbitan fatty ester; poloxamers; ethoxylated polyethylene glycols; ethoxylated, propoxylated, sulphated, phosphated and carbonated acids (and salts), alcohols and their condensates (ester and ether); amine and amide derivatives; aminoacid derivatives; alkylglycoside, lecithin, cholesterol; saponine derivatives. |
| Humectants | 0.00-70.00% | natural and synthetic glycols; lactic acid |
| Emollients | 0.00-70.00% | oils of vegetal origin such as sunflower, corn, soy, nuts and sesame oil; lanolin and its alcohols; fatty acids, fatty alcohols and their condensates (ester and ether) of natural and synthetic origin (below 16 carbons), triglycerides; mineral oil; solid vaselin; silicones; alkanolamides; vegetal butters such as karite, mango, *murumuru*, cupuassu |
| Solvents | 0.00-99.59% | alcohols and/or water |
| Antioxidants | 0.01-10.00% | butyl hydroxide anisol (BHA), butyl hydroxide toluene (BHT), disodium and tetrasodium EDTA; propyl gallate; sodium metabisulphite; natural antioxidants such as tocopherols; phenolic acids; ascorbic acid and its derivatives; citric acid; lecithins; plant extracts such as rosemary and *Lippia* |
| Preserving/ antimicrobial agents | 0.00-10.00% | benzyl alcohol; parabens; benzalkonium chloride; benzethonium chloride; bronopol; cetrimid; chlorobutanol; phenoxyethanol; imidazolidinyl urea; isothiazolinone; hydantoin DMDM; benzoic, sorbic acids and their derivatives; dehydroacetic acid; ferulic acid; natural preserving agents such as essential oils |
| pH correcting agents | 0.10-10.00 | acids and bases of natural and synthetic origin |

Ointment Formulation

| | | |
|---|---|---|
| Active ingredient | 0.10-10.00 | Essential oil of *Lippia salvifolia* and *Lippia sidoides* |
| Thickeners | 0.10-80.00% | fatty acids, fatty alcohols and their condensates (ester and ether) of natural and synthetic origin (above 16 carbons); natural and synthetic waxes such as beewax, candelilla, carnauba and ozokerite; paraffin; natural and synthetic hydrogenated oils; ethoxylated polyethylene glycol |
| Emollients/solvents | 0-99.79% | oils of vegetal origin such as sunflower, corn, soy, nuts and sesame oil; lanolin and its alcohols; fatty acids, fatty alcohols and their condensates (ester and ether) of natural and synthetic origin (below 16 carbons), triglycerides; mineral oil; solid vaselin; silicones; alkanolamides; vegetal butters such as karite, mango, *murumuru*, cupuassu |
| Antioxidants | 0.01-10.00% | butyl hydroxide anisol (BHA), butyl hydroxide toluene (BHT), disodium and tetrasodium EDTA; propyl gallate; sodium metabisulphite; natural antioxidants such as tocopherols; phenolic acids; ascorbic acid and its derivatives; citric acid; lecithins and plant extracts such as rosemary and *Lippia* |
| Preserving/ antimicrobial agents | 0.00-10.00% | benzyl alcohol; parabens; benzalkonium chloride; benzethonium chloride; bronopol; cetrimid; chlorobutanol; phenoxyethanol; imidazolidinyl urea; isothiazolinone; hydantoin DMDM; benzoic, sorbic acids and their derivatives; dehydroacetic acid; ferulic acid; natural preserving agents such as essential oils |

Solution Formulation

| | | |
|---|---|---|
| Active ingredient | 0.10-10.00 | Essential oil of *Lippia salvifolia* and *Lippia sidoides* |
| Emollients/solvents | 0-99.89% | oils of vegetal origin such as sunflower, corn, soy, nuts and sesame oil; lanolin and its alcohols; fatty acids, fatty alcohols and their condensates (ester and ether) of natural and synthetic origin (below 16 carbons), triglycerides; mineral oil; solid vaselin; silicones; alkanolamides; vegetal butters such as karite, mango, *murumuru*, cupuassu |
| Antioxidants | 0.01-10.00% | butyl hydroxide anisol (BHA), butyl hydroxide toluene (BHT), disodium and tetrasodium EDTA; propyl gallate; sodium metabisulphite; natural antioxidants such as tocopherols; phenolic acids, ascorbic acids and their derivatives; citric acid; lecithins and plant extracts such as rosemary and *Lippia* |
| Preserving/ antimicrobial agents | 0.00-10.00% | benzyl alcohol; parabens; benzalkonium chloride; benzethonium chloride; bronopole; cetrimid; chlorobutanol; phenoxyethanol; imidazolidinyl | urea; isothiazolinone; hydantoin DMDM; benzoic, sorbic acids and their derivatives; dehydroacetic acid; ferulic acid; natural preserving agents such as essential oils

The invention claimed is:

1. A phytotherapic pharmaceutical composition in the form of a gel comprising, in weight by percentages:
    0.1-10.00% of essential oil of *Lippia salvifolia* and *Lippa sidoides*;
    0.05-40.00% of at least one component selected from the group consisting of synthetic carboxymethylcellulose polymers; hydroxyethylcellulose and derivatives thereof; polyvinylpirrolidone; polymers and copolymers derived from acrylic acid and polyacrylamide; ethoxylated polyethylene glycol; natural gums; pectin; alginate; aluminum silicate and derivatives thereof; agar; and gelatin;
    1.00-99.73% of at least one component selected from the group consisting of alcohols and water;
    0.10-50.00% of at least one component selected from the group consisting of ethoxylated oils of natural and synthetic origin; derivatives of polyvinyl alcohol; ethoxylated lanolin alcohols; polyoxyethylenes and their derivatives; sorbitan fatty ester; poloxamers; ethoxylated polyethylene glycols; ethoxylated, propoxylated, sulphated, phosphate and carbonated acids and salts, alcohols of quaternary ammonium and their ester and ether condensates; amine and amide derivatives; amino acid derivatives; alkylglycoside; lecithin; cholesterol; and saponine derivatives;
    0.00-10.00% of at least one component selected from the group consisting of benzyl alcohol; parabens; benzalkonium chloride; benzethonium chloride; bronopole; cetrimid; chlorobutanol; phenoxyethanol; imidazolidinyl urea; isothiazolinone; hydantoin DMDM; benzoic acids and their derivatives; sorbic acid and their derivatives; dehydroacetic acid; ferulic acid; natural preserving agents; and essential oils;
    0.00-70.00% at least one component selected from the group consisting of natural and synthetic glycols; and lactic acid;
    0.01-10.00% of at least one component selected from the group consisting of butyl hydroxide anisol (BHA); butyl hydroxide toluene (BHT); disodium and tetrasodium EDTA; propyl gallate; sodium metabisulphite; and antioxidants of vegetal origin;
    0.01-10.00% of at least one component selected from the group consisting of acids and bases of natural and synthetic origin;
    wherein the essential oils of *Lippia salvifolia* and *Lippia sidoides* have a proportional ratio in a range of 9:1 to 1:9, respectively, and contain at least 50% thymol and 5% carvacrol by weight therein.

2. A phytotherapic pharmaceutical composition in the form of a cream comprising, in weight by percentages:
    0.1-10.00% of essential oil of *Lippia salvifolia* and *Lippa sidoides*;
    0.10-70.00% of at least one component selected from the group consisting of fatty acids, fatty alcohols and their ester and ether condensates of natural and synthetic origin above 16 carbons; amide; natural and synthetic waxes; paraffin; ethoxylated polyethylene glycol; hydrogenated natural and synthetic oils; synthetic carboxymethylcellulose polymers; hydroxyethylcellulose and derivatives thereof; polyvinylpirrolidone; polymers and copolymers derived from acrylic acid and polyacrylamide; natural gums; pectin; alginate; aluminum silicate and derivatives thereof; agar; and gelatin;
    0.10-50.00% of at least one component selected from the group consisting of ethoxylated oils of natural and synthetic origin; derivatives of polyvinyl alcohol; ethoxylated lanolin alcohols; polyoxyethylenes and their derivatives; sorbitan fatty ester; poloxamers; ethoxylated polyethylene glycols; ethoxylated, propoxylated, sulphated, phosphate and carbonated acids and salts, alcohols of quaternary ammonium and their ester and ether condensates; amine and amide derivatives; amino acid derivatives; alkylglycoside; lecithin; cholesterol; and saponine derivatives;
    0.00-70.00% at least one component selected from the group consisting of natural and synthetic glycols; and lactic acid;
    0.00-70.00% of at least one component selected from the group consisting of oils of vegetal origin; lanolin and its alcohols; fatty acids, fatty alcohols, and their ester and ether condensates of natural and synthetic origin below 16 carbons; triglycerides; mineral oil; solid vaselin; silicones; alkanolamides; and vegetal butter;
    0.00-99.59% of at least one component selected from the group consisting of alcohols and water;
    0.01-10.00% of at least one component selected from the group consisting of butyl hydroxide anisol (BHA); butyl hydroxide toluene (BHT); disodium and tetrasodium EDTA; propyl gallate; sodium metabisulphite; natural antioxidants; phenolic acids; ascorbic acid and its derivatives; citric acid; lecithins and plant extracts;
    0.00-10.00% of at least one component selected from the group consisting of benzyl alcohol; parabens; bronopole; cetrimid; chlorobutanol; phenoxyethanol; imidazolidinyl urea; isothiazolinone; hydantoin DMDM; benzoic acids and their derivatives; sorbic acid and their derivatives; dehydroacetic acid; ferulic acid; and natural preserving agents;
    0.01-10.00% of at least one component selected from the group consisting of acids and bases of natural and synthetic origin;
    wherein the essential oils of *Lippia salvifolia* and *Lippia sidoides* have a proportional ratio in a range of 9:1 to 1:9, respectively, and contain at least 50% thymol and 5% carvacrol by weight therein.

3. A phytotherapic pharmaceutical composition in the form of an ointment comprising, in weight by percentages:
    0.1-10.00% of essential oil of *Lippia salvifolia* and *Lippia sidoides*;
    0.10-80.00% of at least one component selected from the group consisting of fatty acids, fatty alcohols and their ester and ether condensates of natural and synthetic origin above 16 carbons; natural and synthetic waxes; paraffin; hydrogenated natural and synthetic oils; and ethoxylated polyethylene glycol;
    0.00-99.79% of at least one component selected from the group consisting of oils of vegetal origin; lanolin and its alcohols; fatty acids, fatty alcohols, and their ester and ether condensates of natural and synthetic origin below 16 carbons; triglycerides; mineral oil; solid vaselin; silicones; alkanolamides; and vegetal butter;
    0.01-10.00% of at least one component selected from the group consisting of butyl hydroxide anisol (BHA); butyl hydroxide toluene (BHT); disodium and tetrasodium EDTA; propyl gallate; sodium metabisulphite; natural antioxidants; citric acid; lecithins and plant extracts;

0.00-10.00% of at least one component selected from the group consisting of benzyl alcohol; parabens; benzalkonium chloride; benzethonium chloride; bronopole; cetrimid; chlorobutanol; phenoxyethanol; imidazolidinyl urea; isothiazolinone; DMDM hydantoin; benzoic acids and their derivatives; sorbic acid and their derivatives; dehydroacetic acid; ferulic acid; and natural preserving agents;

wherein the essential oils of *Lippia salvifolia* and *Lippia sidoides* have a proportional ratio in a range of 9:1 to 1:9, respectively, and contain at least 50% thymol and 5% carvacrol by weight therein.

4. A phytotherapic pharmaceutical composition in the form of a solution comprising, in weight by percentages:

0.1-10.00% of essential oil of *Lippia salvifolia* and *Lippa sidoides;*

0.00-99.89% of at least one component selected from the group consisting of oils of vegetal origin; lanolin and its alcohols; fatty acids, fatty alcohols, and their ester and ether condensates of natural and synthetic origin below 16 carbons; triglycerides; mineral oil; solid vaselin; silicones; alkanolamides; and vegetal butter;

0.01-10.00% of at least one component selected from the group consisting of butyl hydroxide anisol (BHA); butyl hydroxide toluene (BHT); disodium and tetrasodium EDTA; propyl gallate; sodium metabisulphite; natural antioxidants; citric acid; lecithins and plant extracts;

0.00-10.00% of at least one component selected from the group consisting of benzyl alcohol; parabens; bronopole; cetrimid; chlorobutanol; phenoxyethanol; imidazolidinyl urea; isothiazolinone; hydantoin DMDM; benzoic acids and their derivatives; sorbic acid and their derivatives; dehydroacetic acid; ferulic acid; and natural preserving agents;

wherein the essential oils of *Lippia salvifolia* and *Lippia sidoides* have a proportional ratio in a range of 9:1 to 1:9, respectively, and contain at least 50% thymol and 5% carvacrol by weight therein.

5. The phytotherapic pharmaceutical composition of claim 1, 2, 3 or 4, wherein the proportional ratio of essential oils of *Lippa salvifolia* and *Lippia sidoides* is around 9:1, respectively.

6. A process for the preparation of a phytotherapic pharmaceutical composition comprising the steps of:

a) drying vegetal material of *Lippia sidoides* and *Lippa salvifolia* in a circulating air oven at about 43° C.;

b) hydrodistillation of the dried vegetal material for a 90-minute period, resulting in a distillate containing *Lippia sidoides* and *Lippa salvifolia* essential oils;

c) separation of the essential oils from the distillate obtained in step b) by decantation;

e) quantitatively analyzing the thymol/carvacrol ratio of the separated essential oils;

f) adding one or more pharmaceutical acceptable carriers and/or excipients to the separated essential oils;

wherein the separated essential oils of *Lippia sidoides* and *Lippa salvifolia* have a proportional ratio in a range of 9:1 to 1:9, respectively, and contain at least 50% thymol and 5% carvacrol by weight therein; and wherein the composition comprises between 0.1 and 10.0% by weight of the separated essential oils.

* * * * *